(12) United States Patent
Cadwell

(10) Patent No.: US 11,273,004 B2
(45) Date of Patent: *Mar. 15, 2022

(54) SYSTEM AND METHOD FOR HIGH DENSITY ELECTRODE MANAGEMENT

(71) Applicant: Cadwell Laboratories, Inc., Richland, WA (US)

(72) Inventor: John A. Cadwell, Richland, WA (US)

(73) Assignee: Cadwell Laboratories, ino., Kennewick, WA (US)

(*) Notice: Subject to any disclaimer, the term of this patent is extended or adjusted under 35 U.S.C. 154(b) by 334 days.

This patent is subject to a terminal disclaimer.

(21) Appl. No.: 16/267,689

(22) Filed: Feb. 5, 2019

(65) Prior Publication Data

US 2020/0000547 A1 Jan. 2, 2020

Related U.S. Application Data

(63) Continuation of application No. 15/376,655, filed on Dec. 12, 2016, now Pat. No. 10,238,467.

(51) Int. Cl.
*A61B 90/98* (2016.01)
*A61B 90/96* (2016.01)
(Continued)

(52) U.S. Cl.
CPC ............ *A61B 90/98* (2016.02); *A61B 5/24* (2021.01); *A61B 5/291* (2021.01); *A61B 5/296* (2021.01);
(Continued)

(58) Field of Classification Search
None
See application file for complete search history.

(56) References Cited

U.S. PATENT DOCUMENTS 6,236,874 B1 5/2001 Devlin
6,805,668 B1 10/2004 Cadwell
(Continued)

FOREIGN PATENT DOCUMENTS

DE 102014008684 A1 1/2016
EP 0863719 A1 9/1998
(Continued)

OTHER PUBLICATIONS

International Search Report for PCT/US2019/063793, dated Feb. 19, 2020.

(Continued)

*Primary Examiner* — Ankit D Tejani
(74) *Attorney, Agent, or Firm* — Novel IP

(57) ABSTRACT

Systems, devices and methods for advanced electrode management in neurological monitoring applications include receiving sockets configured to receive connectors having groups of electrodes. The physician is not required to manually map each electrode with its corresponding input channel. Electrodes are coupled to the corresponding input channels in groups through connectors having a unique identification (ID). The system is configured to read the unique ID of each connector and establish its identity. Based on the ID, the system configures itself to automatically correlate or associate each electrode with its corresponding input channel when the connectors are first inserted into the receiving sockets, and again if the connectors are removed and re-inserted into different positions in the receiving sockets, to insure the electrodes are always mapped to the same input channels.

20 Claims, 13 Drawing Sheets

(51) Int. Cl.
*A61B 5/24* (2021.01)
*A61B 5/291* (2021.01)
*A61B 5/296* (2021.01)
*A61B 5/30* (2021.01)

(52) U.S. Cl.
CPC .............. *A61B 5/303* (2021.01); *A61B 90/96* (2016.02); *A61B 2562/0209* (2013.01); *A61B 2562/046* (2013.01); *A61B 2562/226* (2013.01); *A61B 2562/227* (2013.01)

(56) References Cited

U.S. PATENT DOCUMENTS

| | | |
|---|---|---|
| 6,870,109 B1 | 3/2005 | Villarreal |
| 7,072,521 B1 | 7/2006 | Cadwell |
| 7,230,688 B1 | 6/2007 | Villarreal |
| 7,374,448 B1 | 5/2008 | Jepsen |
| 7,914,350 B1 | 3/2011 | Bozich |
| D670,656 S | 11/2012 | Jepsen |
| 9,155,503 B2 | 10/2015 | Cadwell |
| 9,295,401 B2 | 3/2016 | Cadwell |
| 9,730,634 B2 | 8/2017 | Cadwell |
| 10,238,467 B2 * | 3/2019 | Cadwell .................. A61B 5/291 |
| 2004/0030258 A1 | 2/2004 | Williams |
| 2007/0202005 A1 | 8/2007 | Maschke |
| 2008/0312520 A1 | 12/2008 | Rowlandson |
| 2009/0196471 A1 | 8/2009 | Goetz |
| 2010/0113898 A1 | 5/2010 | Kim |
| 2012/0003862 A1 | 1/2012 | Newman |
| 2013/0012880 A1 | 1/2013 | Blomquist |
| 2014/0121555 A1 | 5/2014 | Scott |
| 2014/0275926 A1 | 9/2014 | Scott |
| 2015/0230749 A1 | 8/2015 | Gharib |
| 2015/0351643 A1 | 12/2015 | Edwards |
| 2015/0372433 A1 | 12/2015 | Lisogurski |
| 2016/0000382 A1 | 1/2016 | Jain |
| 2016/0174861 A1 | 6/2016 | Cadwell |
| 2016/0328991 A1 | 11/2016 | Simpson |
| 2018/0161123 A1 | 6/2018 | Cadwell |

FOREIGN PATENT DOCUMENTS

| | | |
|---|---|---|
| EP | 1182965 B1 | 3/2002 |
| EP | 2173238 A2 | 4/2010 |
| WO | 2016028822 A1 | 2/2016 |

OTHER PUBLICATIONS

International Search Report for PCT/US2017/062559, dated Jan. 26, 2018.

* cited by examiner

SYSTEM AND METHOD FOR HIGH DENSITY ELECTRODE MANAGEMENT

CROSS-REFERENCE

The present application is a continuation application of U.S. patent application Ser. No. 15/376,655, entitled "System and Method for High Density Electrode Management" and filed on Dec. 12, 2016, which is herein incorporated by reference in its entirety.

FIELD

The present specification generally relates to the field of neuro-monitoring applications and more specifically to a system and method for managing a large number of electrodes in such applications.

BACKGROUND

Several medical procedures involve deploying multiple sensors on the human body for the recording and monitoring of data required for patient care. Information, such as vital health parameters, cardiac activity, bio-chemical activity, electrical activity in the brain, gastric activity and physiological data, is usually recorded through on-body or implanted sensors/electrodes which are controlled through a wired or wireless link. Typical patient monitoring systems comprise a control unit connected through a wire to one or more electrodes coupled to the specific body parts of the patient. In some applications, such as with pulse oximeter or EKG (electrocardiograph) devices, the electrodes coupled to the body are easily managed as there are not too many (fewer number of electrodes). However, with applications that require a large number of electrodes to be coupled to the human body, the overall set up, placement and management of electrodes is a cumbersome process.

Neuromonitoring is the use of electrophysiological methods, such as electroencephalography (EEG), electromyography (EMG), and evoked potentials, to monitor the functional integrity of certain neural structures (e.g., nerves, spinal cord and parts of the brain) during surgery. The purpose of neuromonitoring is to reduce the risk to the patient of iatrogenic damage to the nervous system, and/or to provide functional guidance to the surgeon and anesthesiologist. Generally, neuromonitoring procedures such as EEG involve a large number of electrodes coupled to the human body. In an EEG procedure, the electrodes are used to record and monitor the electrical activity corresponding to various parts of the brain for detection and treatment of various ailments such as epilepsy, sleep disorders and coma. EEG procedures are either non-invasive or invasive. In non-invasive EEG, a number of electrodes are deployed on the human scalp for recording electrical activity in portions of the underlying brain. In invasive EEG, through surgical intervention, the electrodes are placed directly over sections of the brain, in the form of a strip or grid, or are positioned in the deeper areas of the brain. Each of these electrodes is coupled to a wire lead which, in turn, is connected to a control unit adapted to receive and transmit electrical signals. The electrical activity pattern captured by various electrodes is analyzed using standard algorithms to localize or spot the portion of brain which is responsible for causing the specific ailment.

The number of electrodes in EEG systems typically varies between 21 and 256. Increasing the number of electrodes in EEG procedures helps decrease the localization error and thus more ably assist the physician to better plan for surgical procedures. Accordingly, advanced EEG systems involve a high density electrode configuration with up to 256 electrodes for separately mapping the electrical activity corresponding to every portion of the brain. However, the overall set up and verification process becomes more time consuming and error prone as the number of electrodes increases in the EEG procedures.

In neuromonitoring, as each electrode is positioned at a different location to capture the electrical activity in its vicinity, the input recorded from each electrode has to be processed independently. The system is required to recognize the identity of each electrode and accordingly process the input received from that electrode. To achieve this, it is important that each electrode is coupled to the correct input channel in the control unit of the neuromonitoring system. However, in practical scenarios, it is possible that, while connecting a large number of electrodes to respective input channels, the medical care provider connects an electrode to a wrong input channel. This could result in making the entire process faulty. Therefore, in high density electrode configurations, the set up process is time consuming as the connection corresponding to each electrode needs to be separately established and then verified for integrity before starting the procedure. In practice, the time required to set up and verify large numbers of connecting leads prevents following the best practice of checking all electrodes and verifying their integrity before starting the procedure and hence compromises the quality of medical care.

Surgical applications in EEG also use grid electrodes which inherently combine multiple leads (up to 16) into a single connector, which is then attached to an adapter with 16 individual leads, and then to an amplifier that has inputs for each individual channel. However, when a patient is monitored with an EEG system having 200+ electrodes, even grouping these electrodes results in more than a dozen adapters and the connections corresponding to these adapters needs to be individually verified every time before starting a procedure.

Therefore, the current neuromonitoring medical devices involving a large number of electrodes do not provide an easy and convenient way for physicians to deploy such systems. These systems suffer from significant risk of unreliable measurements due to incorrect connections. There is significant risk of error in deploying such systems. Further, deployment of such systems is time consuming which prevents following the best practices and therefore compromises the quality of medical care.

Devices and systems are required which are convenient to use and do not consume too much time for deployment. Such devices and systems should automatically recognize the position or identity of various electrodes and associate the electrodes with a specific input channel, thereby not requiring the physician to manually map each electrode with a specific input channel.

SUMMARY

In some embodiments, the present specification discloses a system for neuromonitoring comprising: a plurality of electrode groups wherein each group comprises electrodes, each of said electrodes in each group having at least one of a similar monitoring functionality type and a similar deployment location; a plurality of connectors wherein each connector comprises an electronically accessible memory and wherein a unique identification code is stored in each electronically accessible memory and wherein each electrode group of said plurality of electrode groups is coupled to at least one connector of said plurality of connectors; and, a control unit comprising at least one receiving unit configured for receiving said plurality of connectors, establishing an identity of each connector of said plurality of connectors by identifying each unique identification code associated with each connector of said plurality of connectors, and configuring the system to associate each electrode with a corresponding input channel in the control unit based on said unique identification code.

Optionally, said unique identification code is in a 128 bit GUID format.

Optionally, said at least one receiving unit comprises a plurality of input sockets configured to receive one or more connectors of said plurality of connectors.

Optionally, said one or more connectors are configured to be coupled to any of the plurality of input sockets of said at least one receiving unit.

Optionally, said connector has a designated output pin which is configured to transmit information related to the unique identification code to said control unit.

Optionally, the information related to the unique identification code is formatted as a bar code or a radio frequency code (RFID).

Optionally, the information related to the identification code is stored using multiple pins that are configured as dip switches comprising resistors.

Optionally, each of said plurality of connectors is configured to be inserted in said receiving unit using at least two different orientations.

Optionally, each of said plurality of connectors has two designated output pins which are configured to transmit information related to the unique identification code and an orientation of the connector to said control unit.

Optionally, the two designated output pins are maintained at different polarities or voltage levels to indicate the orientation of the connector as inserted in a receiving unit.

Optionally, a physical position of said two designated output pins is different in each of two orientations.

Optionally, electrodes included in any one electrode group are coupled to inputs of the connector in a predefined order.

Optionally, said electrodes are configured in groups of 4, 6, 8, 10, 12 or 16 electrodes.

Optionally, said system is configured to perform an EEG or EMG procedure.

In some embodiments, the present specification discloses a method for neuromonitoring comprising: providing a plurality of electrodes for deploying on different portions of a human body; arranging said electrodes in a plurality of electrode groups wherein each group comprises electrodes having at least one of a similar monitoring functionality type and a similar deployment location; coupling the electrodes of each one of said plurality of electrode groups with one connector of a plurality of connectors, wherein each connector comprises a unique identification code stored in an electronically accessible memory in said connector; coupling each connector of said plurality of connectors with at least one receiving unit in communication with a system control unit; establishing the identity of each connector of said plurality of connectors from its unique identification code, wherein said receiving unit is configured to establish said identity by identifying each unique identification code associated with each connector of said plurality of connectors; and, configuring the system to associate each electrode with its corresponding input channel in said control unit based on said unique identification code.

Optionally, said unique identification code is in a 128 bit GUID format.

Optionally, said at least one receiving unit comprises input sockets in which one or more said connectors can be inserted.

Optionally, said connectors are connectors are configured to be coupled to any of the inputs of said at least one receiving unit.

Optionally, said connector has a designated output pin which is configured to transmit information related to the unique identification code to said control unit. Optionally, the information related to identification code is communicated through a bar code or a radio frequency code (RFID).

Optionally, each of said plurality of connectors is configured to be inserted in in said at least one receiving unit using at least two different orientations, wherein said at least two different orientations comprise at least a first orientation and at least a second orientation, wherein said second orientation is rotated 180 degrees about a horizontal axis with respect to said at least first orientation.

Optionally, each of said plurality of connectors has two designated output pins which are configured to transmit information related to the identification code and an orientation of the connector to said control unit.

Optionally, the two designated output pins are maintained at different polarities or voltage levels to indicate the orientation of the connector as inserted in a receiving unit.

Optionally, a physical position of said two designated output pins is different in each of said at least two orientations.

Optionally, electrodes included in any one of said group of electrodes are coupled to inputs of the connector in a predefined order.

Optionally, said electrodes are combined in groups of 4, 6, 8, 10, 12 or 16 electrodes.

Optionally, said method is configured to perform an EEG or EMG procedure.

In some embodiments, the present specification is directed toward a medical system for monitoring of patient data comprising: a plurality of electrode groups configured to be attached to a body of a patient wherein each electrode group in said plurality of electrode groups comprises electrodes of a similar type having at least one of a similar monitoring functionality type and a similar deployment location; a plurality of connectors wherein each connector comprises an electronically accessible memory and wherein a unique identification code is stored in each electronically accessible memory and wherein each electrode group of said plurality of electrode groups is coupled to at least one connector of said plurality of connectors; and, a control unit comprising at least one receiving unit configured for receiving said plurality of connectors, establishing an identity of each of said plurality of connectors by identifying each unique identification code associated with each of said plurality of connectors, and configuring the system to relate each electrode with its corresponding input channel in the control unit based on said identification code, wherein relate is defined as placing the electrode in electrical communication with the corresponding input channel.

Optionally, said medical system is configured to be used for neuromonitoring applications.

Optionally, said medical system is configured to be used for an EKG procedure.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout.

DETAILED DESCRIPTION

Figure 1:
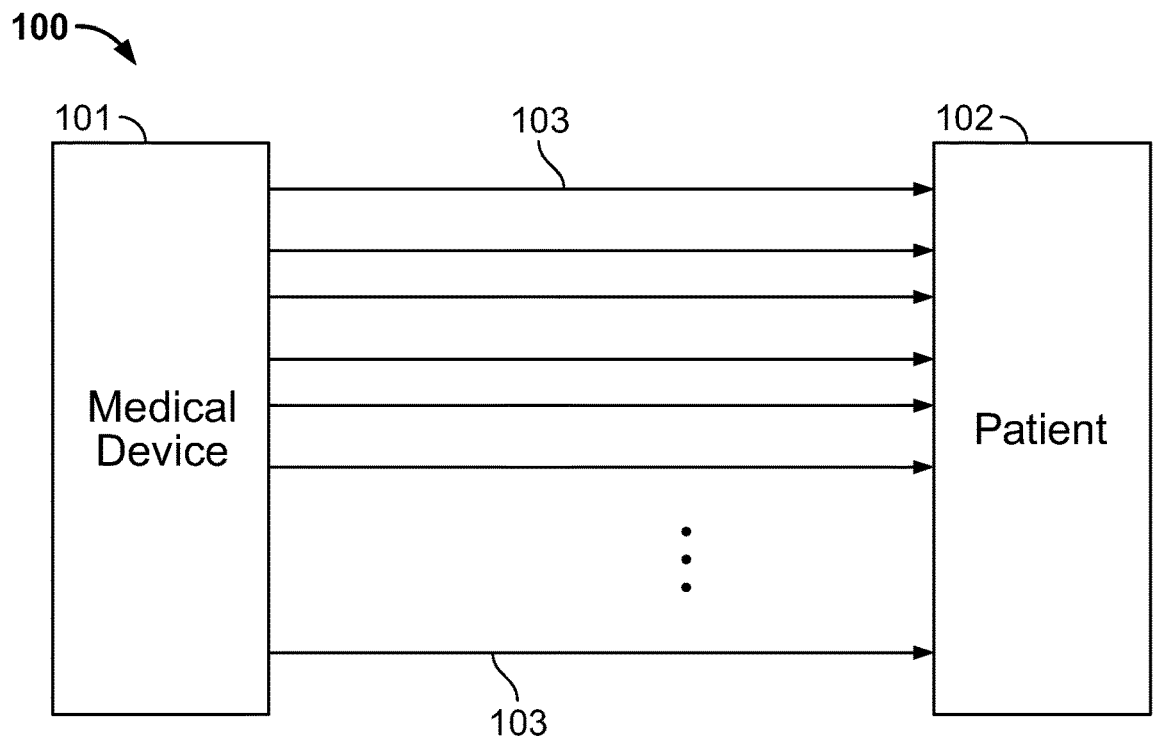
FIG. 1 shows a block diagram of a conventional medical system comprising a large number of electrodes deployed on a patient body.

The system, devices, and methods described below disclose a novel electrode management solution for neuromonitoring applications such as electroencephalography (EEG) procedures. Systems and methods are disclosed which provide a highly reliable and convenient method for electrode management in such applications. In embodiments of the disclosed system, the physician is not required to manually match each electrode lead with its corresponding input channel on the system control unit, significantly reducing the set up time. The electrodes are not directly connected with the input channels in the control unit or the amplifier of the neuromonitoring system. Rather, the control unit is coupled to electrodes with the help of unique connectors and corresponding receiving sockets which enable automatic detection of the electrodes, including their type and deployment location. Once the electrodes are identified, the control unit reconfigures the system to automatically correlate, associate, assign, or 'map', each electrode with its corresponding input channel in the control unit, wherein correlate, associate, assign, relate, or map is defined as placing a specific electrode in electrical communication with the corresponding specific input channel in the control unit. The connectors and receiving sockets insure the control unit will recognize each electrode properly and process information received from each electrode correctly with respect to the electrodes placement position on the patient's body, regardless of where the connector is inserted into the receiving socket.

In embodiments, the electrodes are arranged into a plurality of groups such that the electrodes of similar type, based on their similar monitoring functionality and similar deployment location on a human body, are included in the same group. For purposes of the present specification, the term "similar monitoring functionality" shall mean electrodes that are used for similar neuromonitoring modalities. For example, electrodes used for studies including, but not limited to, electroencephalography (EEG), electromyography (EMG), and evoked potentials are gathered into groups of similar monitoring functionality. Accordingly, all electrodes being used for an EEG constitute electrodes having a similar monitoring functionality and are expressly differentiated from (and therefore do not have similar monitoring functionality as) those electrodes being used for other modalities, such as an EMG. For purposes of the present specification, the term "similar deployment location" shall mean electrodes that are positioned together in a specific area on a patient's head or scalp. For example, electrodes configured to be placed on a front, back, left side, or right side of a patient's scalp would be gathered into groups of similar deployment location based on each area. Accordingly, all electrodes being deployed in front side of a patient's scalp constitute electrodes having a similar deployment location and are expressly differentiated from (and therefore do not have a similar deployment location as) those electrodes being deployed on the back side, left side, or right side of the patient's scalp, each of those being different deployment locations.

Subsequently, each group of electrodes is mapped to a separate connector in a pre-defined order and all such connectors are coupled with a receiving socket on the system control unit. When a group of electrodes are mapped to a connector, the exact position and type of each electrode in that group is standardized, as the electrodes are coupled to a connecter in a pre-defined order, and the connector is assigned a unique identification code or ID. The connectors and the receiving sockets have an identity (ID) read capability such that when any connector is inserted in the receiving socket, the receiving socket can identify the connector from its unique identification code or ID and based on the identity of the connector, the specific location and type of all the electrodes mapped to this connector are established. The ID information is carried explicitly by the connector, and not implicitly by the receptacle. The ID information is stored in electronically accessible memory on the connector. In various embodiments, the memory is any one or combination of non-volatile memory, such as read-only memory (ROM), programmable read-only memory (PROM), erasable programmable read-only memory (EPROM), and electronically erasable programmable read-only memory (EEPROM), and volatile memory, such as dynamic random-access memory (DRAM) and static random-access memory (SRAM). The electrodes of a group and the connector are never separated, and if the connector is reinserted elsewhere on an array of available inputs, the system will remap the inputs to the correct channels. The ID information is for all electrodes in a group, which, in some embodiments, is 16 at a time, compared to one electrode at a time which is encountered in current systems. The information needed to determine where the electrode is attached is a function of both the connector (using its unique ID) and either a pre-defined setup (for example, in the case of a 10/20 system headcap) or a setup specified on a per connector basis by the user to a computer system.

In embodiments, when a connector is coupled with a receiving socket, the medical system requests for the information on the electrodes coupled to each input of that connector. The user subsequently provides information on the various electrodes coupled to the specific inputs of the connector. In an embodiment, the user manually inserts this information (or selects the data from a list of available options) through an electronic keyboard or keypad coupled with the medical system. Once the user provides this information, the exact position and type of each electrode in a group coupled with a specific connector is standardized. In some alternate embodiments, the standardized information related to exact order in which electrodes are coupled to each connector is provided to the medical system before inserting the connectors in the receiving socket.

The receiving socket comprises a bank of input points and is configured such that various connectors having unique IDs and representing separate groups of electrodes can be inserted in any of the inputs on the receiving socket. Once the receiving socket establishes an electrical connection with a connector, it can read the unique ID of the connector to establish its identity. On establishing the identity of the connector, the system is able to recognize the type and specific location of various electrodes mapped to the connector.

Using the concept of connectors with unique ID as disclosed herein, the position of the electrodes in a specific group is standardized with respect to the connector. The electrodes from the same group are coupled to inputs of the connector in a pre-defined sequence and the system reading the unique ID of the connector assigns the correct meaning (electrode type and location) to each input. The medical care provider has to just take care that the electrodes corresponding to a single connecter are mapped in the same pre-defined sequence or order before each procedure. Once identified, the electrode groups can be removed and reinserted in any available slot without error. The system will note the new connection and assign the correct meaning to the input. Handling electrode leads in small groups makes the entire set up process less cumbersome in case of high density electrode applications, such as EEG procedures involving over 200 electrodes. In conventional systems, if the electrical connectors corresponding to electrodes are removed and reinserted into receptacles located within the medical device, each electrical connector has to be reinserted into exactly the same receptacle or the electrode body site to channel display will be incorrect. However, in the above disclosed system, the user can remove the various connectors from the medical device and can reinsert these connectors in any of the input points in the receiving sockets.

An exemplary beneficial use of the connector systems of the present specification is with an MRI procedure. During an MRI, the monitoring system amplifier inputs need to be disconnected from the amplifier itself as the amplifier is not allowed into the intense magnetic fields generated by the MRI machine. Disconnecting and reconnecting 200 leads for such a procedure is time consuming and error prone. Such a laborious process can preclude the use of an MM procedure, even if it is the preferred imaging technique. If an amplifier fails, the leads would need to be moved. In a set of 200 non-identified individual leads, the process is not only error prone, but each channel would have to be remapped manually, and in some systems, the channels have to be used consecutively, so the 'abandoned' channels continue to be displayed. In the identified connector systems of the present specification, there is less chance for error in reconnecting the leads and the process is much quicker.

It should be noted herein that any feature or component described in association with a specific embodiment may be used and implemented with any other embodiment unless clearly indicated otherwise.

FIG. 1 show a block diagram of a conventional medical system 100 comprising a large number of electrodes deployed on a patient 102 body. The medical device 101 represents any conventional neuromonitoring medical system which comprises a large number of electrodes, such as an EEG (electroencephalography) system, which is used for monitoring the neurological state of a patient for diagnosis and preventive treatment of certain diseases and for monitoring patients during anesthesia, among other procedures. As shown in FIG. 1, the medical device 101 is coupled to the patient 102 through a plurality of electrical leads 103 such that each of the leads 103 is coupled to an electrode (not shown) positioned at an appropriate location on the body of the patient. In applications that require a large number of electrodes to be coupled to the human body, the setup, placement and management of electrodes is a cumbersome process. As each electrode is positioned at a different location to capture the electrical activity in its vicinity, the input recorded from each electrode has to be processed independently. Therefore, the system is required to recognize the identity of each of the electrical leads 103 and accordingly process the input received from it. After positioning any electrode at its required location on the body of the patient 102, the user is required to correctly insert the electrode lead 103 corresponding to each electrode in a specific input channel configured for that electrode in the medical device 101. In case the number of electrodes is small, for example, less than ten or fifteen, it is possible for the user to identify and connect electrodes with the correct input channels. However, as the number of electrodes increases, this process become very difficult and is prone to error. Further, even if the electrodes are coupled to the correct input slots in the medical device 101, it is practically very difficult and time consuming to recheck and verify the integrity of each connection before every procedure. Usually, in such high density configurations, the set up process is so time consuming that in some circumstances, for example during a surgical procedure, the user completely or partially skips the step of checking each connection for integrity until after the surgery is finished, which increases the possibility of error in the procedure.

Figure 2:
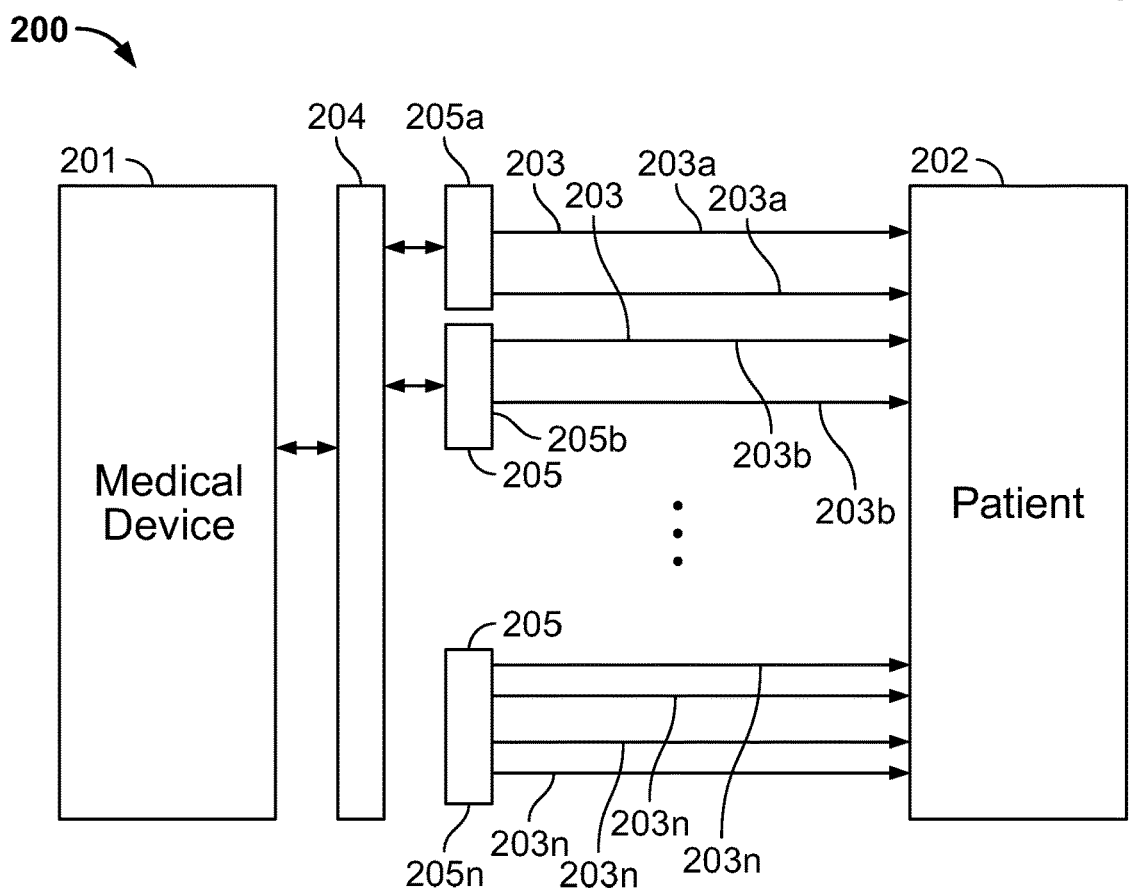
FIG. 2 shows a block diagram of an illustrative medical system comprising a large number of electrodes deployed on the body of a patient as disclosed in accordance with an embodiment of the present specification.

FIG. 2 shows a block diagram of an illustrative medical system 200 comprising a large number of electrodes deployed on the body of a patient 202 as disclosed in an embodiment. The medical device 201 comprises a number of electrodes (not shown) coupled to the body of the patient 202 through a plurality of electrical leads 203. In neuro-monitoring medical procedures such as EEG, the electrodes come in groups such that the electrodes in a specific group have similarities in terms of their input signal and positioning. In the systems and methods described herein, the electrodes and the corresponding electrical leads 203 are also arranged in a plurality of groups such as 203a, 203b, . . . , 203n such that each of these groups comprises electrodes of similar type and location and is configured independently. In the disclosed arrangement, instead of directly connecting the medical device 201 with the deployed electrodes, the electrodes are arranged in groups and each group is coupled to the medical device 201 through a connector 205 having a unique ID. Each of the groups of electrical leads 203a, 203b, . . . , 203n (representing electrodes of similar type and location) is coupled to a corresponding connector 205a, 205b, . . . , 205n such that the group of electrical leads 203a is coupled to the connector 205a, the group of electrical leads 203b is coupled to the connector 205b, and similarly the group of electrical leads 203n is coupled to the connector 205n. The various connectors 205a, 205b . . . , 205n are connected with a receiving socket 204 which is coupled to the medical device 201. The receiving socket 204 comprises a bank of inputs and is configured to receive the connectors 205a, 205b, . . . , 205n in any of these inputs. Each of the connectors 205a, 205b, . . . , 205n has an independent identity and the receiving socket 204 is configured to establish the identity of any such connector when the same is connected with it. By establishing the identity of any connector 205, the system 200 is able to identify the various electrodes, including their type and location, coupled to each connector 205. All the electrodes coupled to a single connector 205 belong to the same group and are hence interchangeable in terms of their signal conditioning requirements. The anatomic positions of the patient connected electrodes coupled to the corresponding electrical leads 203 are always in the same defined input sequence on connector 205. Further, as the receiving socket 204 is configured to identify any connector 205 from its unique ID and, therefore, the group of electrodes coupled to that connector 205, the connectors can be plugged into any of the inputs in receiving socket 204.

In an embodiment, the connectors 205a, 205b, . . . , 205n comprise a designated pre-defined identification output point/pin such that, when any connector is plugged into the receiving socket 204, the receiving socket 204 reads the information received from the output pin to establish the identity of the connector 205. Once the identity of a connector 205 is established, the system 200 recognizes the set of electrodes mapped with that connector 205 and reconfigures itself to automatically correlate, associate or map each electrode with its corresponding input channel.

Using the concept of handling electrodes in independent groups as described above, instead of manually mapping each electrode with its corresponding input channel in the medical device 201, the user only needs to ensure that the electrodes belonging to the same group are coupled to the same connector in the same order. This occurs by default when the inputs are part of a mechanically defined grid or strip. Subsequently, the user can insert multiple such connectors in a receiving socket in any of its inputs. The disclosed method significantly reduces the set up time required before starting any medical procedure as the conventional process of manually mapping electrodes with input channels is very tedious and time consuming. Disclosed systems and methods also reduce the risk of error by obviating the human involvement in mapping of electrodes with corresponding input channels.

The number of electrodes coupled to any of the connectors 205 can vary and is dependent on the actual medical requirement. Usually, the electrodes which are deployed in the similar location and receive similar input signal can only be grouped and coupled to a single connector. In medical procedures such as an EEG, the electrodes come in groups of 4, 5, 6, 8, 10 and 16 electrodes, wherein each such group is targeted towards a specific part of the brain. In such cases, multiple different sized connectors are deployed which are capable of supporting the above mentioned groups of electrodes.

Figure 3A:
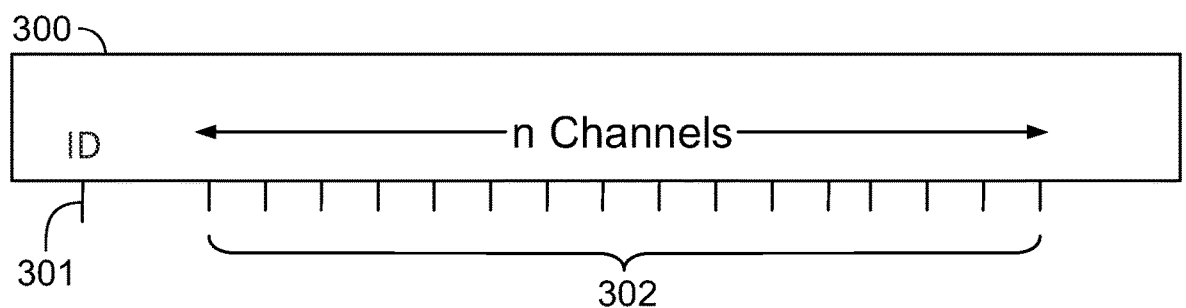
FIG. 3A shows an exemplary connector and a receiving socket in accordance with an embodiment of the present specification.
Figure 3A:
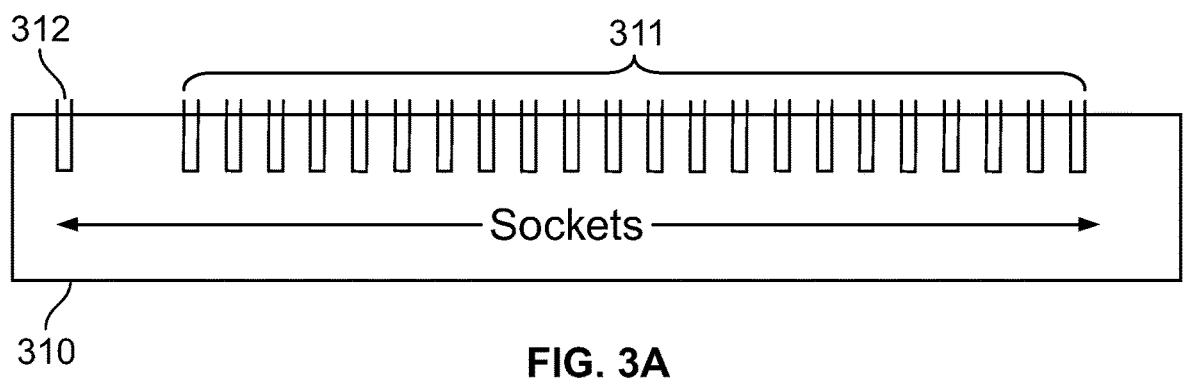

FIG. 3A shows an exemplary connector 300 and a receiving socket 310 in an embodiment. As shown in FIG. 3A, the connector 300 comprises a plurality of signal output pins 302 which corresponds to a plurality of electrodes (not shown) deployed on the body of the patient with the help of the connector 300. The connector 300 is coupled to the plurality of electrodes through one or more electrical leads (not shown). In some embodiments, the connector 300 is coupled to the electrodes through a wireless communication link. In embodiments, each connector, such as the connector 300, has a unique identity and is coupled to a plurality of electrodes which are included in the same group. When the electrodes are classified in the same group, it means their input signals are of the same type and their relative positions are fully defined. These electrodes are connected to the input terminals of the connector in a specific pre-defined order. FIG. 3A shows an 'n' channel connector 300, which means that the connector 300 can accommodate an electrode group with maximum number of n electrodes wherein n is any natural number. In commercial applications, the value of n is usually 4, 6, 8, 10, 12 and 16, such that the corresponding number of electrodes can be coupled to a single connector.

In an embodiment, the connector 300 comprises a specific identification (ID) output pin 301 which is used to establish the unique identity (ID) of the connector 300. The receiving socket 310 comprises a bank of signal input points or sockets 311 which are configured to receive the signal output pins 302 of the connector 300. Usually, a receiving socket, such as the receiving socket 310, comprises enough input points to receive multiple connectors. In practical applications involving high density electrodes, the number of input points is over 200. The receiving socket 310 is coupled to a control unit/amplifier (not shown) which is used to control the entire system. In an embodiment, the receiving socket 310 comprises a separate ID input socket 312 which is configured to receive the ID output pin 301 of the connector 300. The connector 300 is inserted in the receiving socket 310 such that the ID output pin 301 is received in the ID input socket 312 and the signal output pins 302 are received in a subset of signal input sockets 311. Referring to FIG. 3A, in some embodiments, the system includes a plurality of receiving sockets 310 and a plurality of connectors 300 wherein any connector 300 can be inserted into any receiving socket 310 such that the ID output pin 301 aligns with and inserts into a corresponding ID input socket 312.

Once the identity of the connector 300 is established, the system is able to identify the type and location of all the electrodes coupled to the connector 300 irrespective of the set of input sockets 311 in which the connector 300 is inserted. Once the electrodes are identified, the control unit coupled to the receiving socket 310 reconfigures the system to automatically correlate, associate, assign or map each electrode with its corresponding input channel.

Each of the connectors, such as the connector 300, has a unique ID (identity). This identification information is stored in the connector 300 and is accessible to the system from its identification (ID) output pin 301. The ID information specifies the type and relative location of each electrode in the connector 300. In embodiments, the ID field comprises a GUID (Globally Unique Identifier) which is a standard format comprising 128-bit data and is used as an identifier in the computer software. It may also contain other device specific information about the attached device. Once a GUID is assigned, each input can be uniquely identified thereafter. In embodiments, the GUID data is stored in an inbuilt memory device in the connector 300 and, optionally, the memory device is an EPROM storage device. In some embodiments, the GUID is a digital ID which stores additional metadata with the electrode such as checksums, productions dates and authenticity. In other embodiments, the same electrode information is stored using multiple pins used like dip switches (combinations=2**n, i.e. 3 connections would give 8 combinations), with a resistor whose value represents the input type (i.e. 10 combinations per resistor), with a multiple pin multiple resistor (100 combinations with 2 pins), or with a bar code that could be read automatically. In other embodiments, the identification information is communicated through an RFID stored in the connector.

In the embodiment shown in FIG. 3A, the connector 300 is shown as a male electrical connector and the corresponding receiving socket 310 is shown as a female electrical connector. In other embodiments, the connector is configured as a female connector and the receiving socket is configured as a male connector.

Figure 3B:
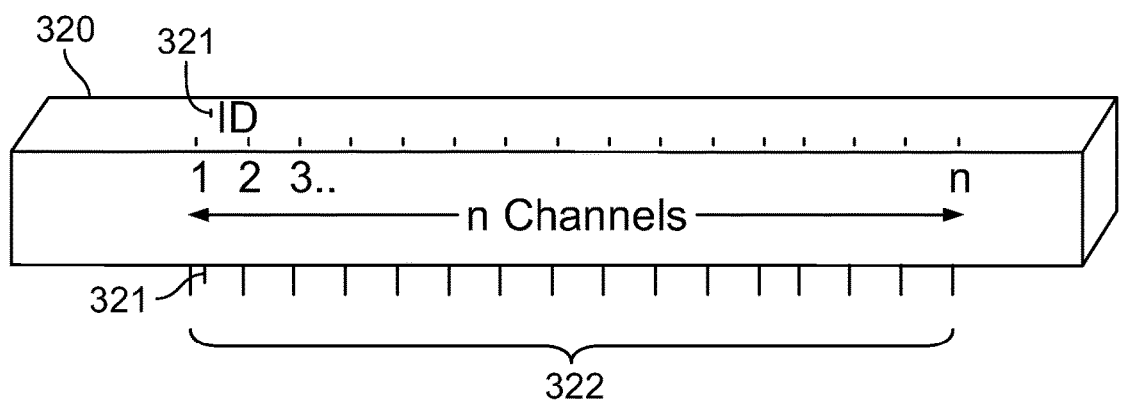
FIG. 3B shows an exemplary connector and a receiving socket in accordance with another embodiment of the present specification.
Figure 3B:
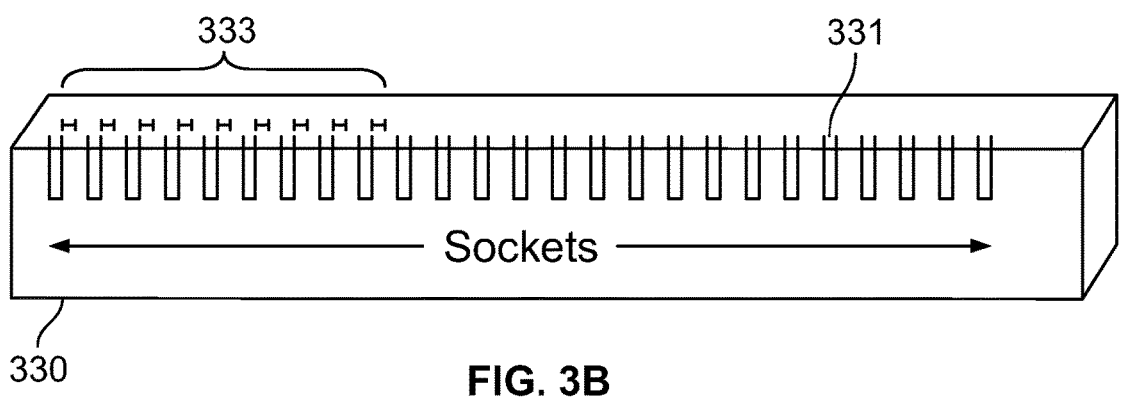

In another embodiment shown in FIG. 3B, the connector 320 is configured such that the ID output pin 321 is aligned parallel to, but not in series with, the set of signal output pins 322. The corresponding receiving socket 330 is configured such that instead of only one ID input socket, the receiving socket 330 comprises a plurality of ID input sockets 333 which are aligned parallel to the set of signal input sockets 331. The connector 320 and the receiving socket 330 shown in FIG. 3B are configured such that the connector 320 can be inserted in any of the input sockets 331 provided the ID output pin 321 is received by at least of the ID input sockets 333.

In medical procedures, the electrodes are classified in groups wherein the electrodes belonging to the same group are of similar type and are deployed in a similar location. In EEG procedures, the electrodes come in groups of 4, 5, 6, 8, 10 and 16 electrodes, wherein each such group is targeted towards a specific part of the brain. If connectors of the same size are used for all electrode groups, several input channels will go to waste in the case of connectors that are mapped to groups having fewer numbers of electrodes. To allow high utilization of input channels, in embodiments, the electrodes are organized in small groups and the connectors are designed in different sizes which provide the flexibility to support the electrode groups of varying sizes.

Figure 4:
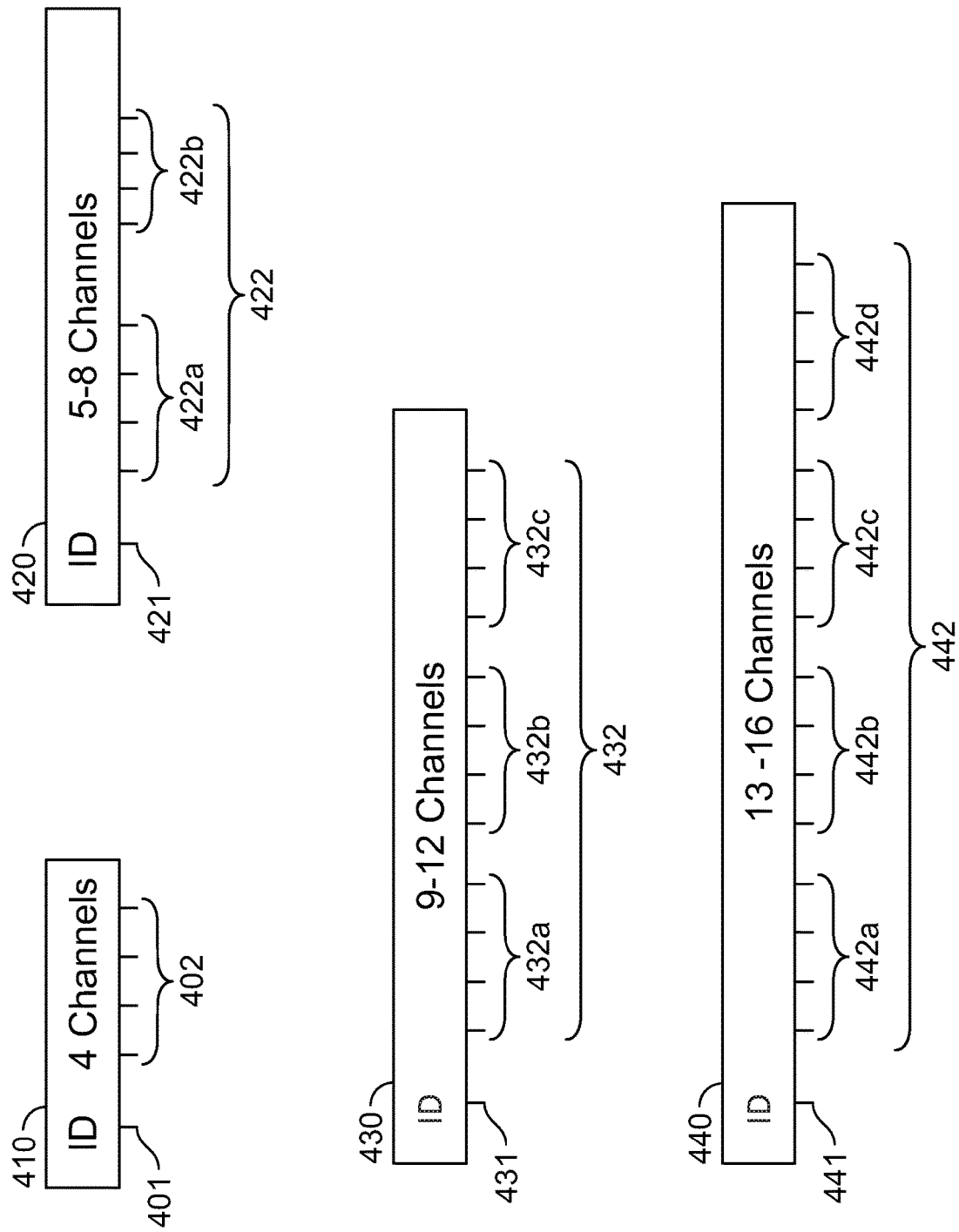
FIG. 4 shows an illustration of connectors of different sizes in accordance with various embodiments of the present specification.

FIG. 4 shows an illustration of connectors 410, 420, 430, 440 of different sizes. As shown in FIG. 4, connector 410 comprises an ID output pin 401 and a set of four output pins 402 which can support an electrode group comprising up to four electrodes. Connector 420 comprises eight output pins 422 so in case the number of electrodes is more than four and less than or equal to eight, the user can deploy connector 420 instead of the connector 410. Similarly, connector 430, having 12 output pins can support up to 12 electrodes and connector 440, having 16 output pins, can support up to 16 electrodes. Connectors 420, 430, and 440 also include ID output pins 421, 431, and 441 respectively. Instead of using connectors of a single size, the user can deploy connectors of multiple sizes, thereby reducing the space requirement in actual procedures. All the connectors have an ID output pin 401, 421, 431, 441 which is used to identify the unique identity of a connector which the system will use to correlate, assign, or associate all electrodes mapped through a connector with their correct channels. In some embodiments, referring to connectors 420, 430, and 440, the output pins are grouped into groups of four channels. For example, connector 420 includes two four-pin groups 422a and 422b of output pins 422, connector 430 includes three four-pin groups 432a, 432b, and 432c of output pins 432, and connector 440 includes four four-pin groups 442a, 442b, 442c, and 442d of output pins 442. A receiving socket is capable of accepting any of the connectors to be plugged in anywhere along its bank of inputs. Each connector needs only a single ID and the socket is configured to identify any connector in any position.

In embodiments, connectors and the corresponding receiving socket comprise mechanisms to ensure that there is no misalignment when the connector is coupled with the receiving socket. In embodiments, multiple connector types are provided to be used with different kinds of products. In embodiments, certain inputs of the connectors are provided with enhanced capabilities, such as lower noise, higher offset voltage tolerance or differential inputs, and the user is required to plug inputs needing such capabilities into a subset of connector locations. In some embodiments, not every input has the same requirements and the amplifier or signal processing needed is different for those inputs. If the physical connector is inserted into an input whose channel did not support the function, then the system could notify the user to choose a different input that did support the function. In some embodiments, the system includes a subset of channels that have more capability and could accept either normal or enhanced inputs. These channels would still support non-enhanced inputs to allow better channel utilization. In some embodiments, $SpO_2$ or otherwise not supported input types are configured to a small number of inputs. In other embodiments, pressure inputs, for example, plug into a different bank of identified connectors set up for pressure measurements instead of voltage measurements.

In embodiments, apart from the unique ID, certain other information is stored in the connectors, such as the authentication information, production dates of the connector and the electrodes corresponding to each connector.

Figure 5A:
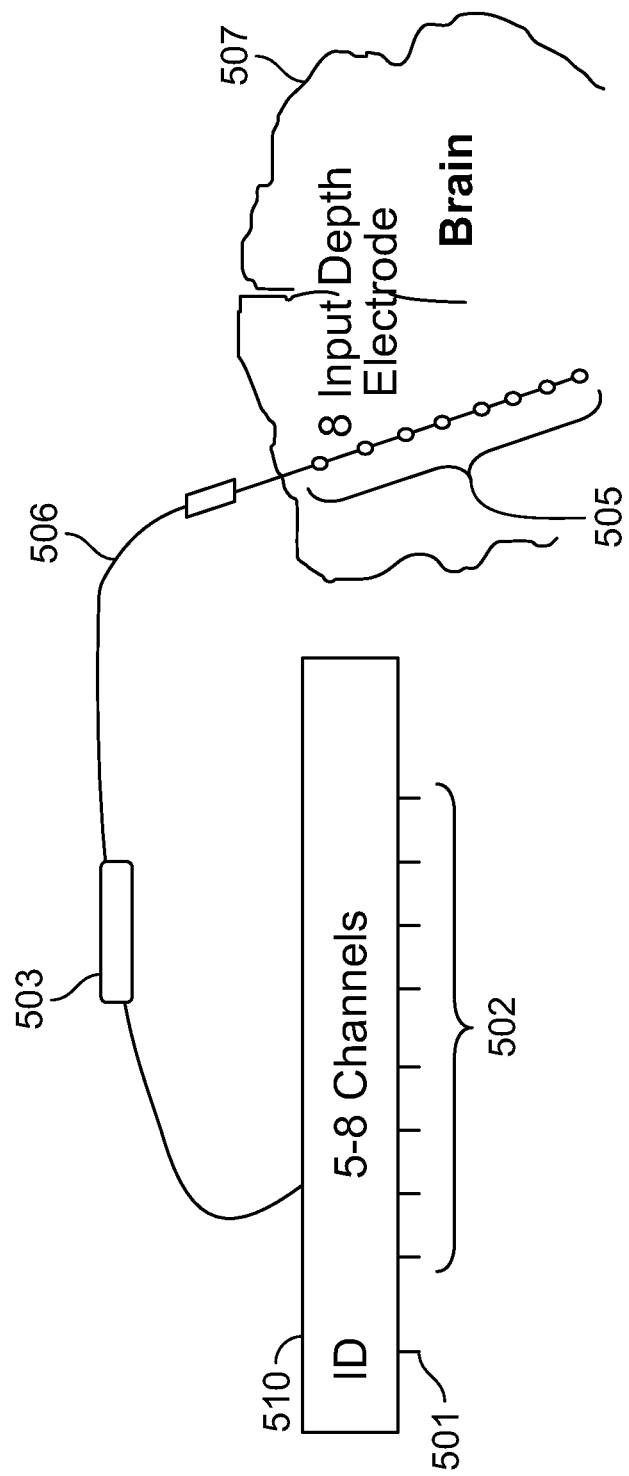
FIG. 5A shows an exemplary illustration of an eight channel connector deployed to support an eight input depth electrode in an EEG procedure in accordance with an embodiment of the present specification.

FIG. 5A shows an exemplary illustration of an eight channel connector 510 deployed to support an eight input depth electrode 505 in an EEG procedure. As shown in FIG. 5A, the connector 510 comprises an ID output pin 501 and a set of eight output pins 502 which means that the connector 510 can support up to eight electrodes. The connector 510 is coupled to an eight input depth electrode 505 through a set of electrical leads 506. In some embodiments, the depth electrode 505 is coupled to the connector 510 via one or more intermediate connectors 503, 504. The intermediate connectors 503, 504 provide the system with greater flexibility when dealing with the limited geometry involved in surgical procedures. In other embodiments, the system does not include intermediate connectors and the electrodes couple directly with the connector and the ID information is very specific to the electrode (for example, electrode caps, respiratory belts, and EKG inputs). The depth electrode 505 is positioned in the cortex area of the brain 507. The connector 510 has a unique ID (identity) stored in an inbuilt memory. In an embodiment, the unique ID comprises a 128 bit GUID and is stored in an EPROM (erasable programmable read-only memory) device in the connector 510. When the connector 510 is plugged in a receiving socket, the system reads the ID information from the EPROM memory device through ID output pin 501 and establishes the identity of the eight input depth electrode 505 coupled to the connector 510. The system accordingly configures itself (and reconfigures itself if the connectors are removed and re-inserted in another position) to correlate or associate the correct inputs of the depth electrode 505 with their corresponding input channels.

Figure 5B:
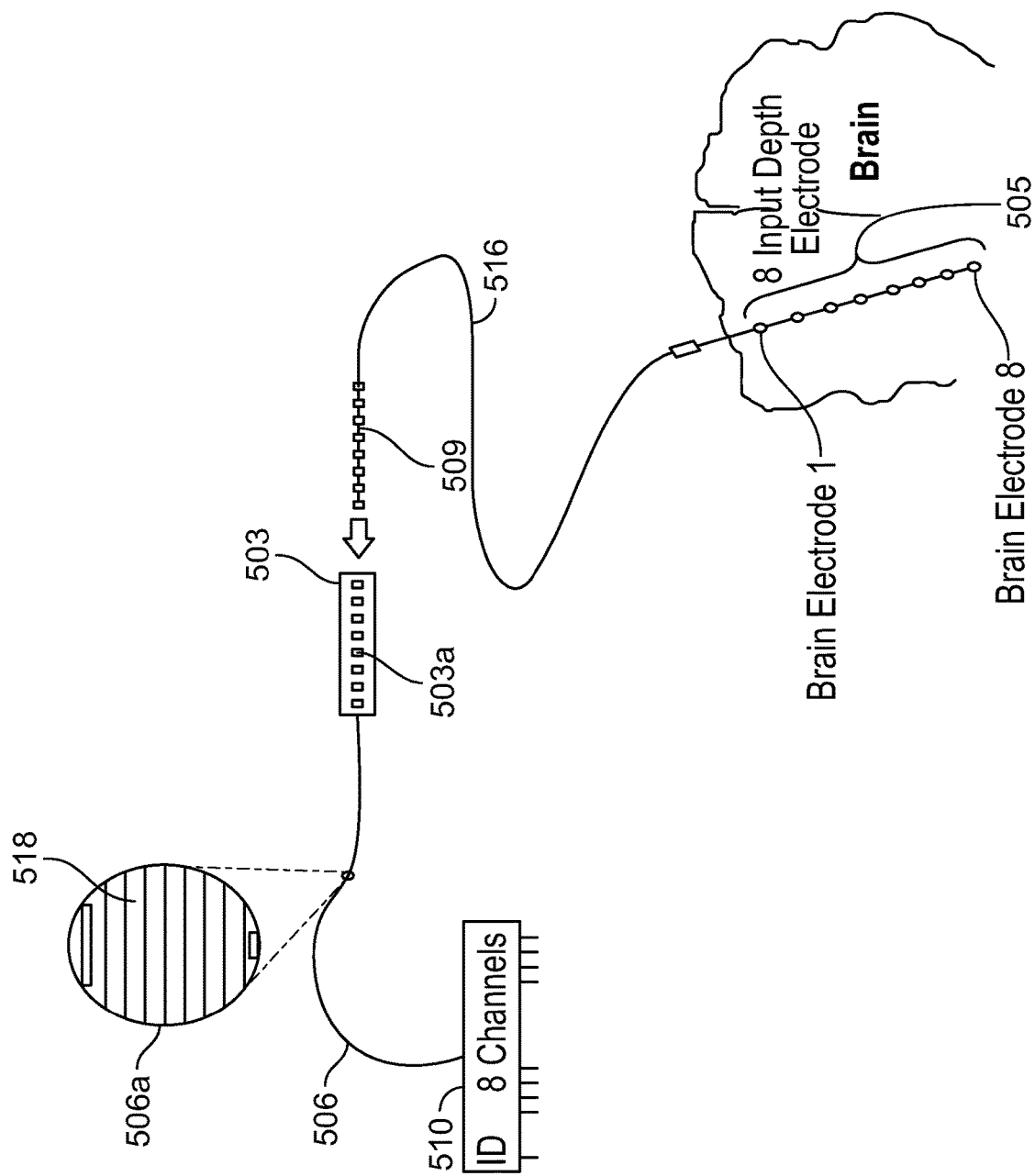
FIG. 5B shows a detailed illustration of the eight channel connector deployed to support an eight input depth electrode in an EEG procedure as depicted in FIG. 5A.

FIG. 5B shows a detailed illustration of the eight channel connector 510 deployed to support an eight input depth electrode 505 in an EEG procedure as depicted in FIG. 5A. As shown in FIG. 5B, the connector 510 is coupled to the depth electrode 505 through an electrical lead 506. In FIG. 5B, the intermediate connector 503 comprises a ring contact connector which is configured to receive a wire 516 with multiple ring contacts such that each ring contact is coupled to one of a plurality of inputs of the eight input depth electrode 505. The wire 516 comprises a set of ring contacts 509 such that as the wire 516 is inserted into the intermediate connector 503, each of these ring contacts 509 establishes an electrical contact with one of the eight ring shaped receptacles 503*a* in the intermediate connector 503. The electrical lead 506 comprises multiple conductors 518 inside it wherein each such conductor 518 acts as a separate electrical communication channel between the depth electrode 505 and eight channel connector 510. An exploded view of the lead 506 is shown as 506*a* which comprises eight different electrical conductors 518. As described above, the intermediate connector 503 uses ring contact receptacles and provides the system with greater flexibility in dealing with electrodes, such as the depth electrode 505. In some embodiments, connector 503 is used in different configurations.

Figure 6:
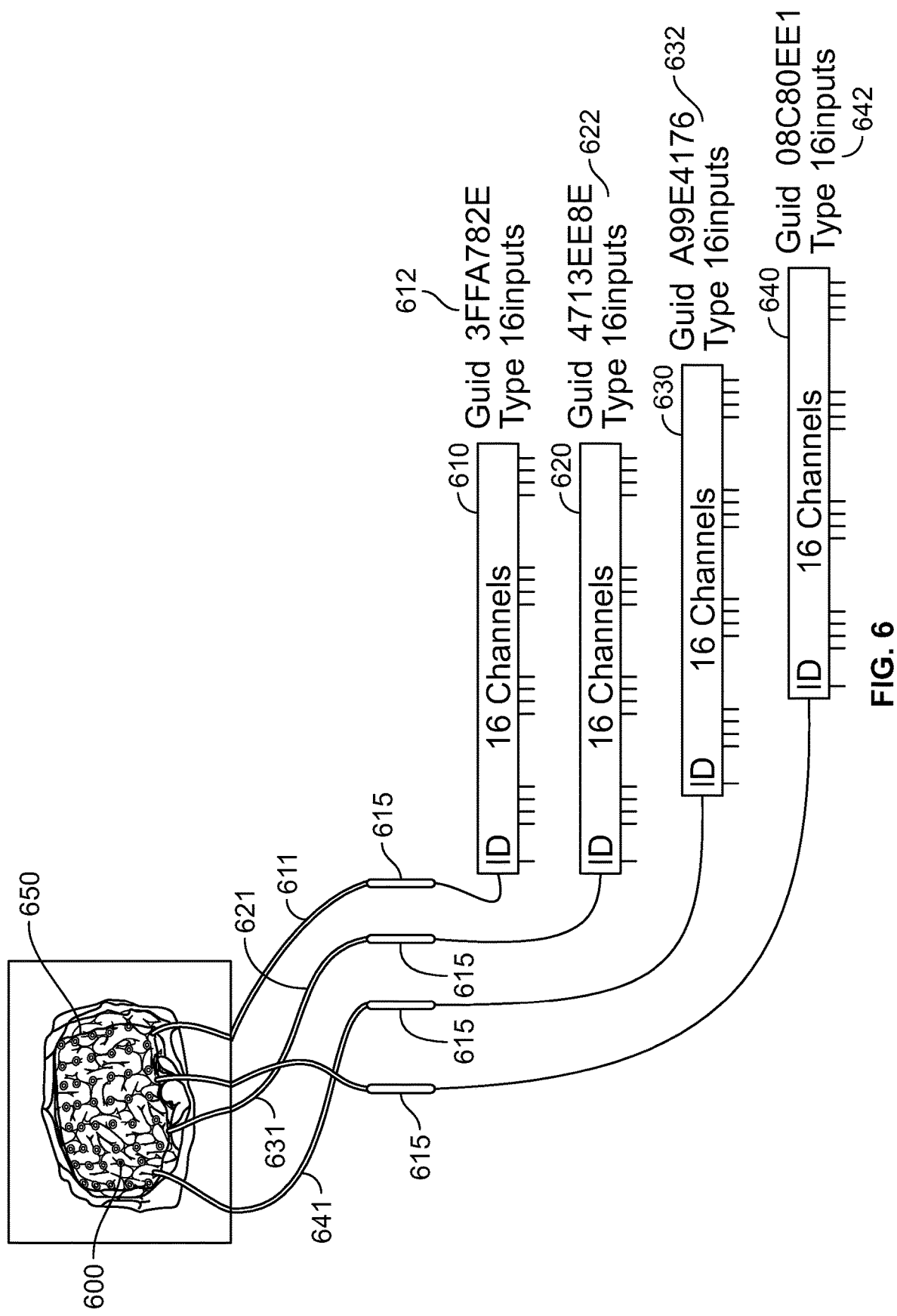
FIG. 6 shows a 64 electrode grid deployed on the brain using connectors in accordance with an embodiment of the present specification.

FIG. 6 shows a 64 electrode grid 600 deployed on a brain 650 using the connectors disclosed in this specification. As shown in FIG. 6, the electrode grid 600 comprises 64 electrodes which are deployed on various portions of the brain 650. The electrode grid 600 is deployed through an invasive surgery. The 64 electrodes are arranged in four groups with each group comprising 16 electrodes. The first group of 16 electrodes is coupled to a 16 channel connector 610 through a first electrical lead 611. The second group of 16 electrodes is coupled to a 16 channel connector 620 through a second electrical lead 621. The third group of 16 electrodes is coupled to a 16 channel connector 630 through a third electrical lead 631. The fourth group of 16 electrodes is coupled to a 16 channel connector 640 through a fourth electrical lead 641. In some embodiments, each lead 611, 621, 631, 641 is connected to its respective connector 610, 620, 630, 640 via an intermediate connector 615. The intermediate connectors 615 provide the system with greater flexibility when dealing with the limited geometry involved in surgical procedures. Each of the connectors 610, 620, 630 and 640 has a unique ID which is stored in an inbuilt memory in the corresponding connector. In an embodiment, the ID of various connectors comprises a 128 bit GUID which can be read by the system when the corresponding connector is plugged in a receiving socket of the system control device. Connector 610 comprises a first GUID 612, connector 620 comprises a second GUID 622, connector 630 comprises a third GUID 632 and connector 640 comprises a fourth GUID 642. When any of the connectors 610, 620, 630 and 640 is plugged in a receiving socket, the system reads its GUID information and establishes the identity of connector. Subsequently, the system configures itself to correlate or associate the electrodes mapped to the corresponding connector with the correct input channels.

Figure 7:
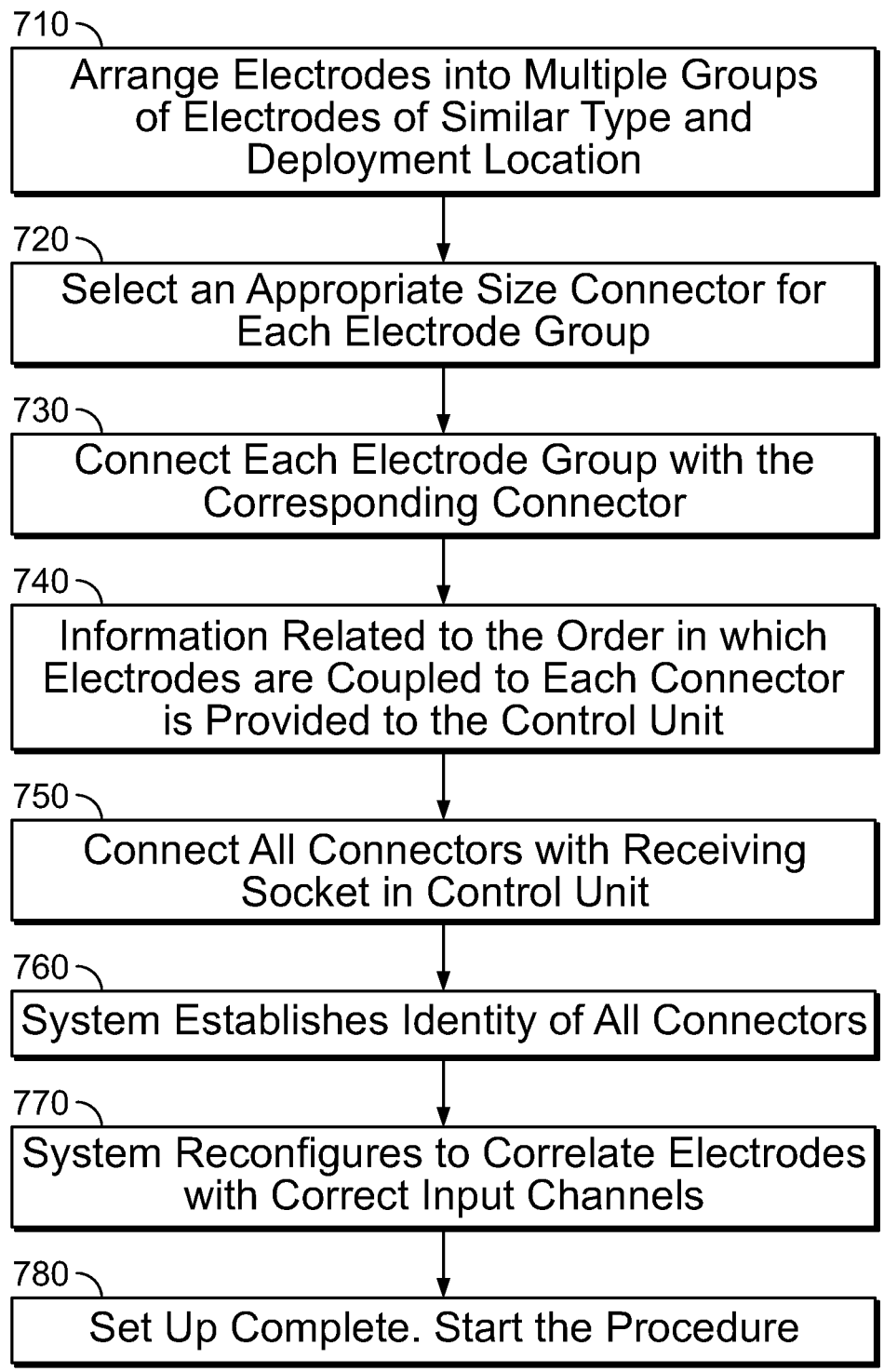
FIG. 7 shows a flowchart illustrating the steps performed in a method of configuring an electrode connection system in accordance with one embodiment of the present specification.

FIG. 7 shows a flowchart illustrating the steps involved in one embodiment of configuring a system using the connectors disclosed in the present specification. As shown in FIG. 7, at step 710, the electrodes are arranged into a plurality of groups such that electrodes of similar type and deployment location are included in the same group. The electrodes in the same group have similarities in terms of their input channel and positioning and are coupled to the same connector in a specific sequence.

At step 720, based on the number of electrodes in each group, a connector of appropriate size is selected for each electrode group. The connector should have a number of input channels greater than or equal to the number of electrodes in the electrode group supported by it. At step 730, electrodes are connected with the corresponding connectors. At step 740, the information related to the order in which the electrodes are coupled to each connector is provided to the control unit. At step 750, the connectors are connected with a receiving socket in the control unit of the medical device. At step 760, the system establishes the identity of all connectors using the unique ID information stored in each connector. At step 770, the system configures itself to correlate or associate each electrode with its corresponding input channel in the control unit. At step 780, the system set up is complete and procedure can be started. In some embodiments, step 740 is executed after step 750 when the system requests for information about the electrode group coupled with a connector at a run time after a connector is inserted in the receiving socket and the user subsequently provides this information to the control unit.

Figure 8A:
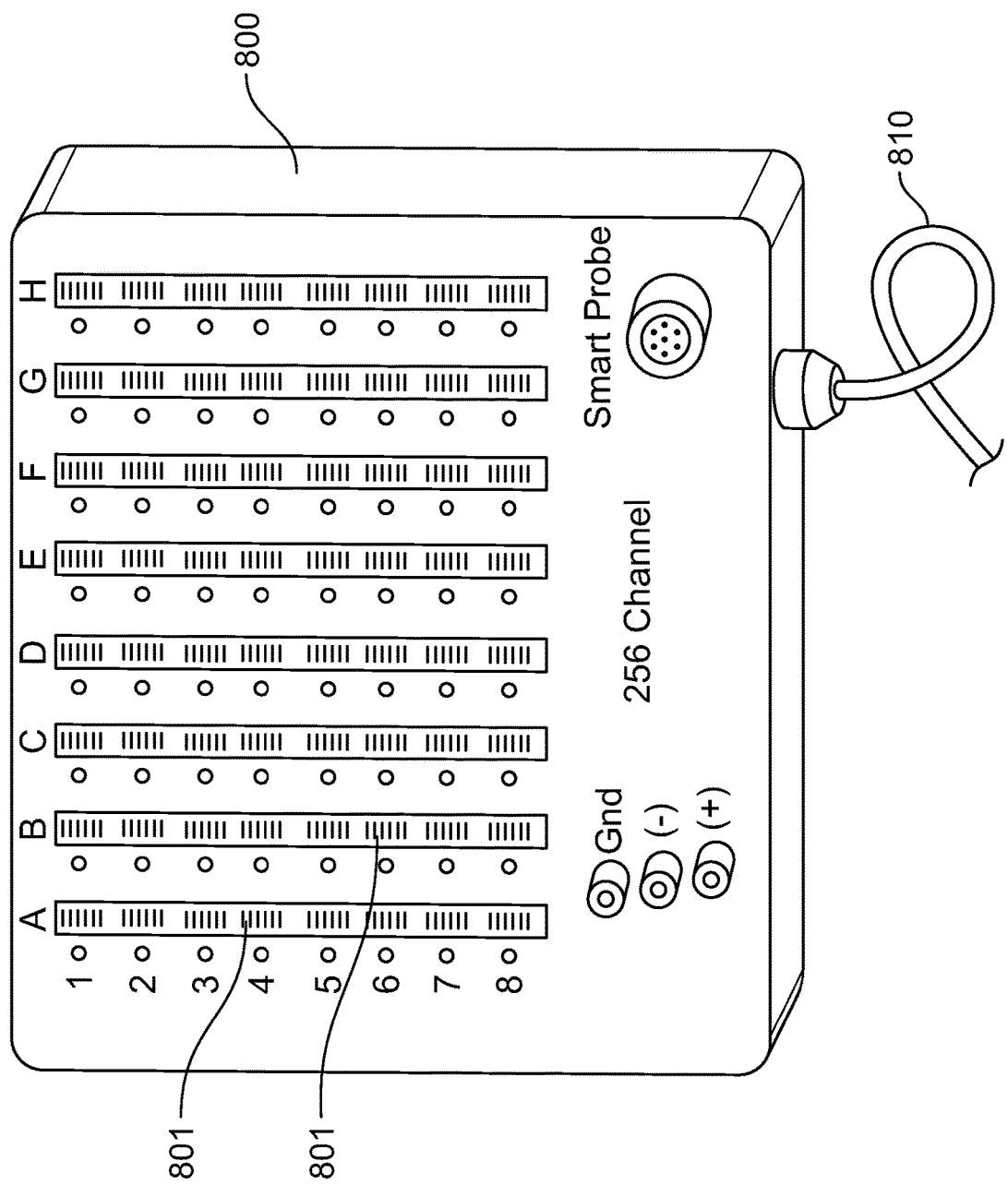
FIG. 8A shows a control unit of a 256 channel neuromonitoring EEG system having receiving sockets which are configured to receive multiple connectors, in accordance with an embodiment of the present specification.
Figure 8B:
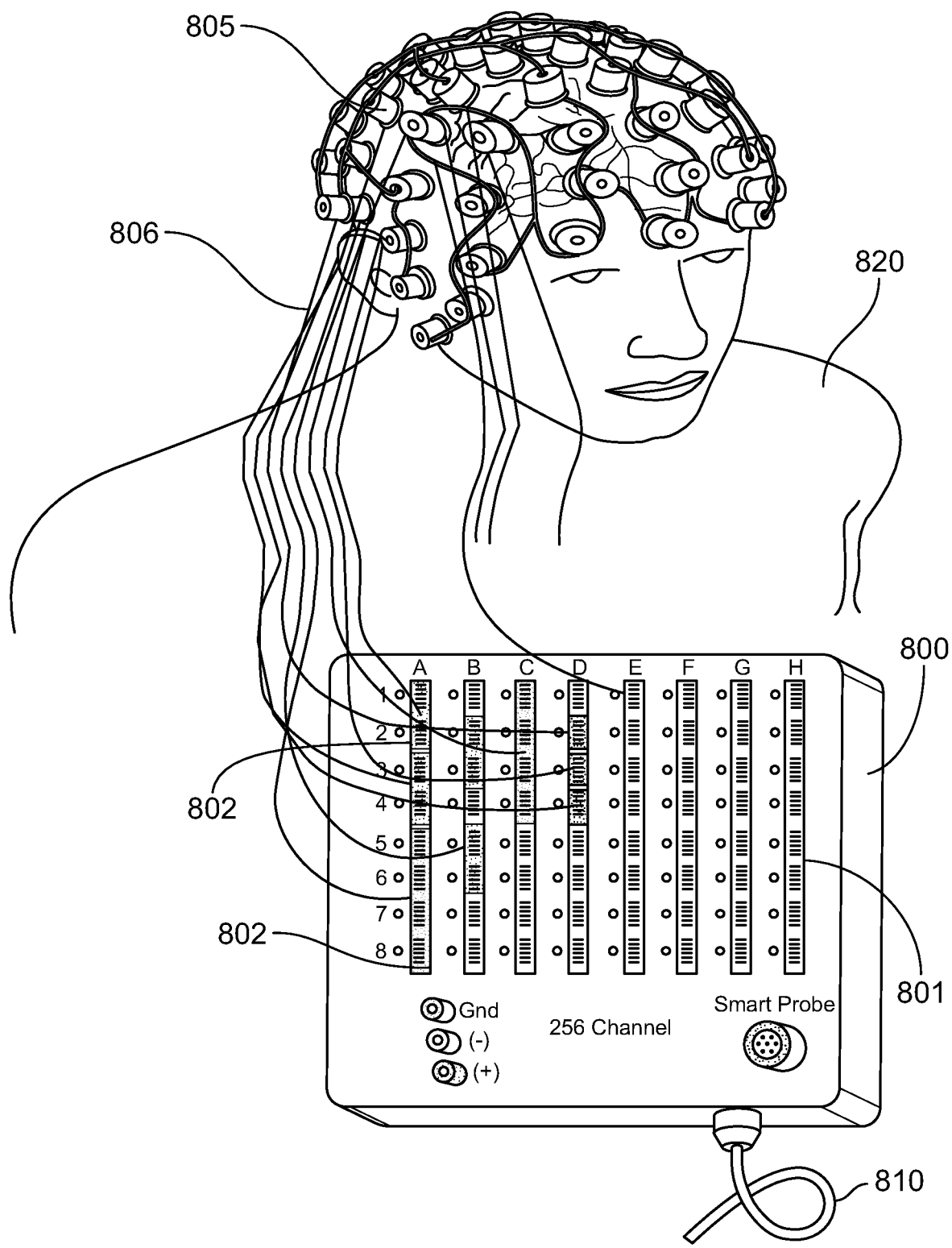
FIG. 8B shows the system of FIG. 8A being used for monitoring the neurological state a patient.

FIG. 8A shows a control unit 800 of a 256 channel neuromonitoring EEG system having receiving sockets 801 which are configured to receive multiple connectors. As shown in FIG. 8A, the control unit 800 of the medical system comprises a plurality of receiving sockets 801. The control unit 800 comprises 256 input channels and can therefore support the same number of electrodes. In control unit 800, the receiving sockets 801 corresponding to the 256 input channels are divided into eight columns such that each column corresponds to 32 input channels. The control unit 800 is coupled to a data acquisition system through cable 810. FIG. 8B shows the medical system of FIG. 8A being used for monitoring the neurological state of a patient. As shown in FIG. 8B, a plurality of electrodes 805 are positioned over the head of a patient 820 to monitor the electrical activity of brain. The electrodes 805 are arranged into groups such that each group comprises electrodes of same type. These multiple groups of electrodes are coupled to separate connectors, such as the connectors 410, 420, 430, and 440 shown in FIG. 4. The electrodes 805 are coupled to connectors 802 though a plurality of electrical leads 806. The connectors 802 are coupled to the receiving sockets 801 as shown in FIG. 8B. Each of the connectors 802 has a unique identity which is stored in the connector in the form of a GUID. The receiving sockets 801 are configured to read the GUID information of each connector and establish its identity. After establishing the identity of connectors 802, the control unit 800 configures the system to correlate or associate each of the electrodes 805 with its corresponding input channel in the control unit 800.

In various embodiments, the connectors and receiving sockets of the systems of the present specification are 'keyed' in such a way so that the connectors can be inserted into the receiving sockets at several locations, but cannot be inserted backwards or at an invalid location. For example, in some embodiments, a connector is configured such that it can be inserted in a top-up or bottom-up orientation, with respect to its horizontal axis, into a receiving socket, but only at discrete locations in the receiving socket. In an embodiment, the receiving socket is configured to detect the orientation of the connector and the ID of the connector. In another embodiment, the pins are duplicated on both top and bottom sides of the connector. Some embodiments of keyed connector and receiving socket connections are described with reference to FIGS. 9A through 11 below and are intended to be exemplary in nature and not limiting with respect to the present specification.

Figure 9A:
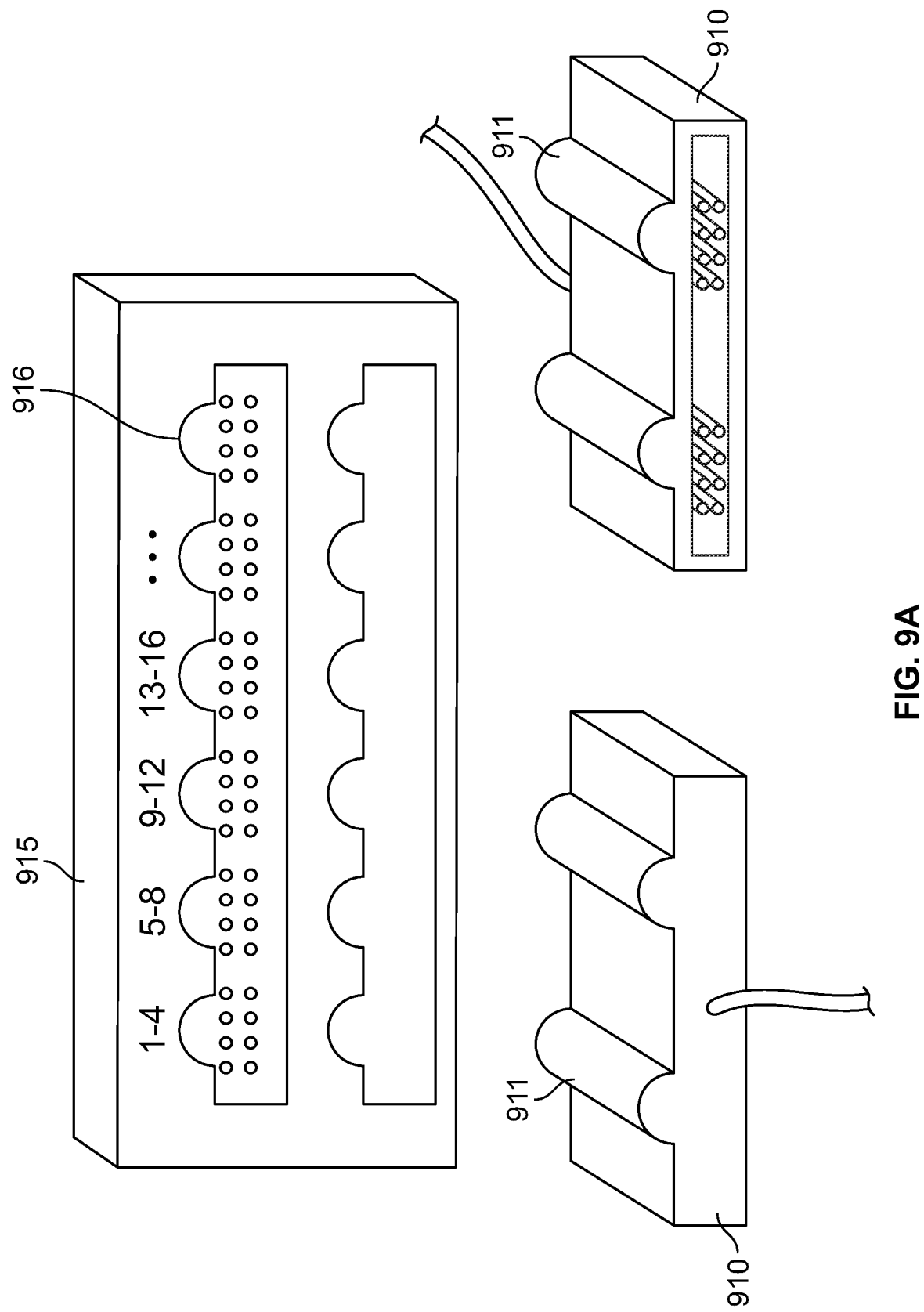
FIG. 9A shows an illustration of an exemplary connector and receiving socket in accordance with various embodiments of the present specification.
Figure 9B:
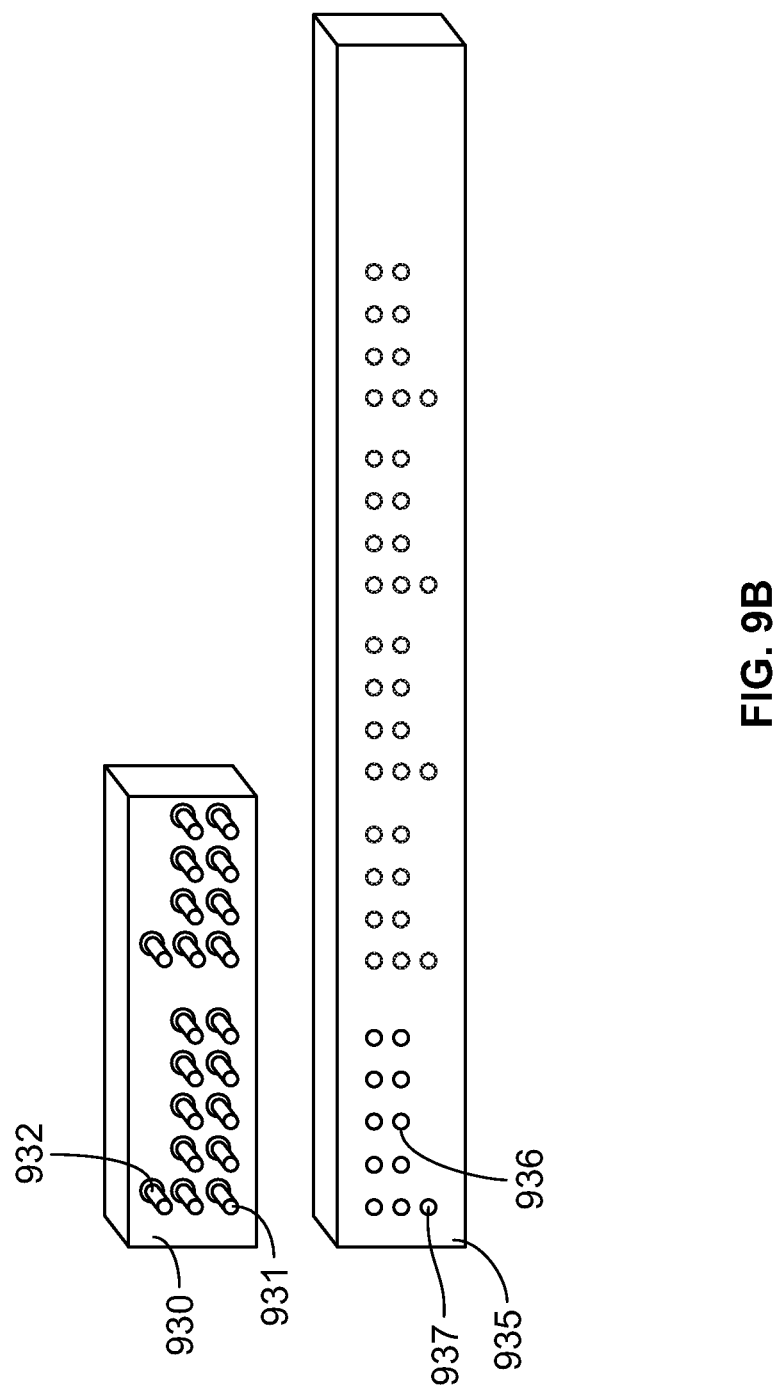
FIG. 9B shows another illustration of an exemplary connector and receiving socket in accordance with other embodiments of the present specification.

FIG. 9A and FIG. 9B show an illustration of exemplary embodiments of connectors 910, 930 and receiving sockets 915, 935. The connectors 910, 930 and receiving sockets 915, 935 are configured with design features to allow for only one orientation during connection. Referring to FIG. 9A, connector 910 includes a pair of 'keys' or ridges 911 at its top surface with align with notches 916 in the receiving socket 915 to ensure the connector 910 is inserted correctly into the receiving socket 915. In embodiments, the connector 910 has one design element, such as the ridge 911, for every four signal input pins and the receiving socket 915 has multiple notches, such as the notch 916, such that the connector 910 can be received at multiple locations along the receiving socket 915 occupying 4, 8, 12, or 16 input sockets. In the above embodiment, the connector 910 comprises one design element or ridge 911 and the receiving socket has one notch 916 for every four number of signal input pins. In other embodiments, the number of signal input pins corresponding to each design element or ridge 911 is of a different multiple, for example, 5, 6, or 7, and the notch 916 of the receiving socket 915 is configured accordingly to support the corresponding structure of the connector 910.

Referring to FIG. 9B, the connector 930 is provided with an asymmetric distribution of pins 931 which corresponds with a matching asymmetric distribution of receptacles 936 on the receiving socket 935 to ensure the connector 930 is inserted correctly into the receiving socket 935. As depicted in FIG. 9B, an ID output pin 932 on the connector 930 is positioned separate from the set of pins 931 and aligns with an ID input socket 937 separate from the set of receptacles 936 on the receiving socket 935 to ensure proper alignment and identification.

Figure 10:
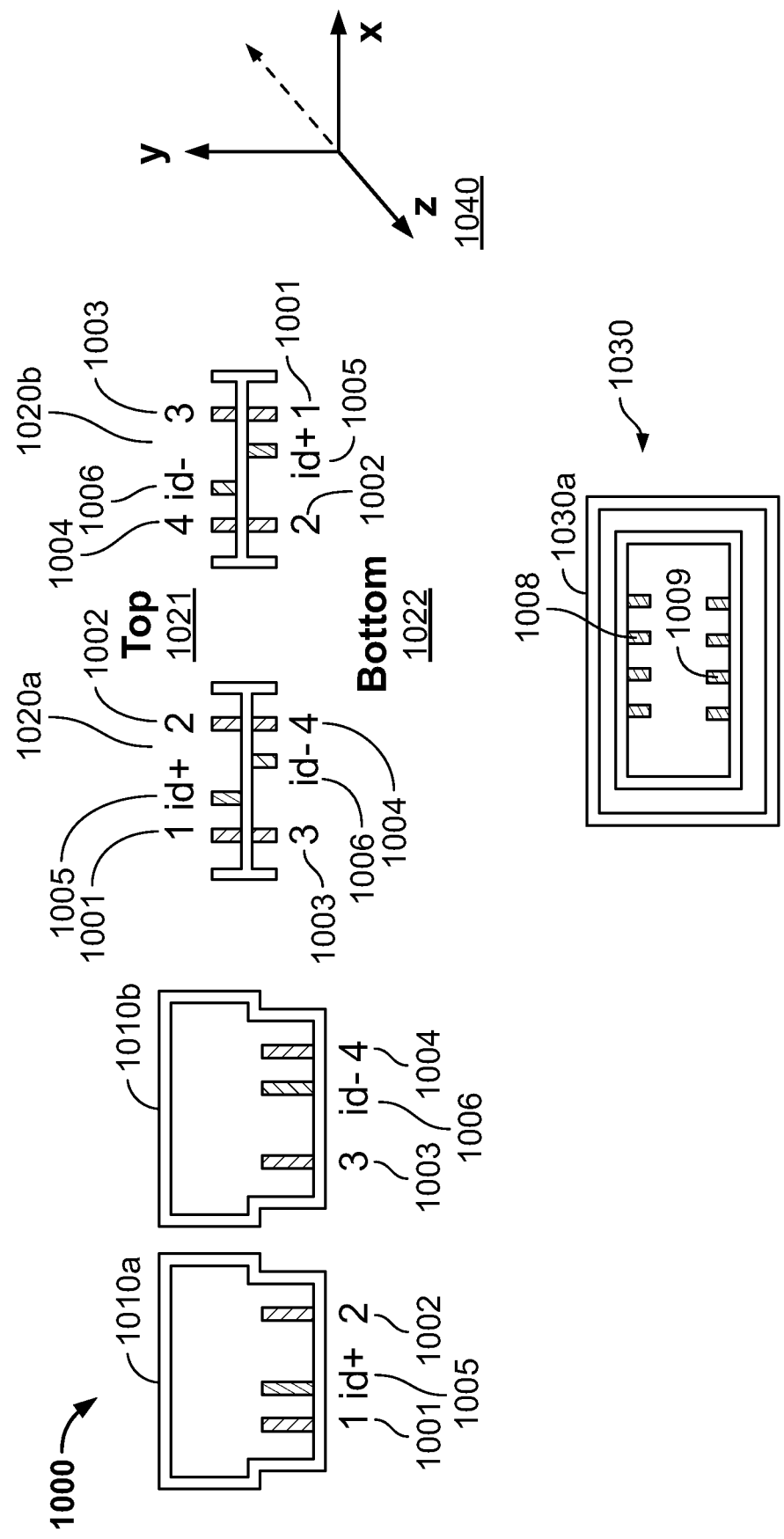
FIG. 10 illustrates a connector which can be used in dual orientations in accordance with an embodiment of the present specification.

FIG. 10 illustrates a connector 1000 which can be used in dual orientations in accordance with an embodiment of the present specification. A first side 1010a and a second side 1010b of a connector 1000 are depicted in FIG. 10. In an exemplary embodiment, the connector 1000 comprises four output signal pins 1001, 1002, 1003 and 1004 and two ID pins 1005 and 1006. The first side 1010a comprises the output signal pins 1001 and 1002 and the ID pin 1005. The second side 1010b comprises the output signal pins 1003 and 1004 and the ID pin 1006.

The connector 1000 can be coupled to the receiving unit or socket 1030 in two different orientations. A first front-on view 1020a depicts the first side 1010a of the connector 1000 oriented to a 'top' surface 1021 and the second side 1010b oriented to a 'bottom' surface 1022. View 1020a of the connector 1000 depicts the positioning of the various output signal pins and the ID pins in a first orientation, with output signal pins 1001 and 1002 and ID pin 1005 positioned on said 'top' surface 1021 and output signal pins 1003 and 1004 and ID pin 1006 positioned on said 'bottom' surface 1022. A second front-on view 1020b depicts the second side 1010b of the connector 1000 oriented to said 'top' surface 1021 and the first side 1010a oriented to said 'bottom' surface 1022. View 1020b depicts the positioning of the various output signal pins and the ID pins in a second orientation, with output signal pins 1003 and 1004 and ID pin 1006 positioned on said 'top' surface 1021 and output signal pins 1001 and 1002 and ID pin 1005 positioned on said 'bottom' surface 1022. In the second view 1020b, the connector 1000 is rotated 180 degrees about its horizontal axis or Z axis 1040 as compared to its position in the first view 1020a.

As shown in FIG. 10, the first and the second views 1020a, 1020b of connector 100, respectively depicting first and second configurations, are horizontally flipped images of each other, about the Z axis 1040, and hence it is not possible to distinguish one orientation from another from the physical structure. In the disclosed system, the receiving unit 1030 detects the orientation of the connector 1000 based on the polarities of the ID pins. In FIG. 10, the two ID pins 1005, 1006 have opposite polarities such that ID pin 1005 has a positive polarity and ID pin 1006 has a negative polarity. In other embodiments, ID pin 1005 has the negative polarity and ID pin 1006 has the positive polarity. When the connector 1000 is inserted in the receiving unit 1030, depicted in a front-on view 1030a, the various output signal pins and the ID pins of the connector 1000 establish contact with the various input mating sockets or pins in the receiving unit 1030. When the connector 1000 is inserted in the receiving unit 1030 in the first orientation, as shown in view 1020a, the ID pin 1005 establishes contact with the ID input pin 1008 and the ID pin 1006 establishes contact with the ID input pin 1009 of the receiving unit 1030. Alternatively, when the connector 1000 is inserted in the receiving unit 1030 in the second orientation, as shown in view 1020b, the ID pin 1006 establishes contact with the ID input pin 1008 and the ID pin 1005 establishes contact with the ID input pin 1009 of the receiving unit 1030. The system reads the respective polarities of the ID pins in contact with the ID inputs sockets 1008 and 1009 and hence detects the orientation of the connector 1000 as inserted in the receiving socket 1030. Subsequently, the system reconfigures itself to automatically map each input with its corresponding input channel.

The system disclosed in FIG. 10 uses two ID pins with opposite polarities. In some embodiments, the polarities of the two ID pins are not opposite and the two ID pins are just maintained at different voltage levels and the identity of the ID pins is detected based on the signal/voltage received from the corresponding ID pins. Once the system identifies and distinguishes the two ID pins, the orientation of the connector as inserted in the receiving socket is detected. The system disclosed in FIG. 10 comprises four output signal pins, however, in other embodiments, the number of output signal pins present in the connector is different, such as less than 4 or greater than 4, including 5, 6, 7, or more.

Figure 11:
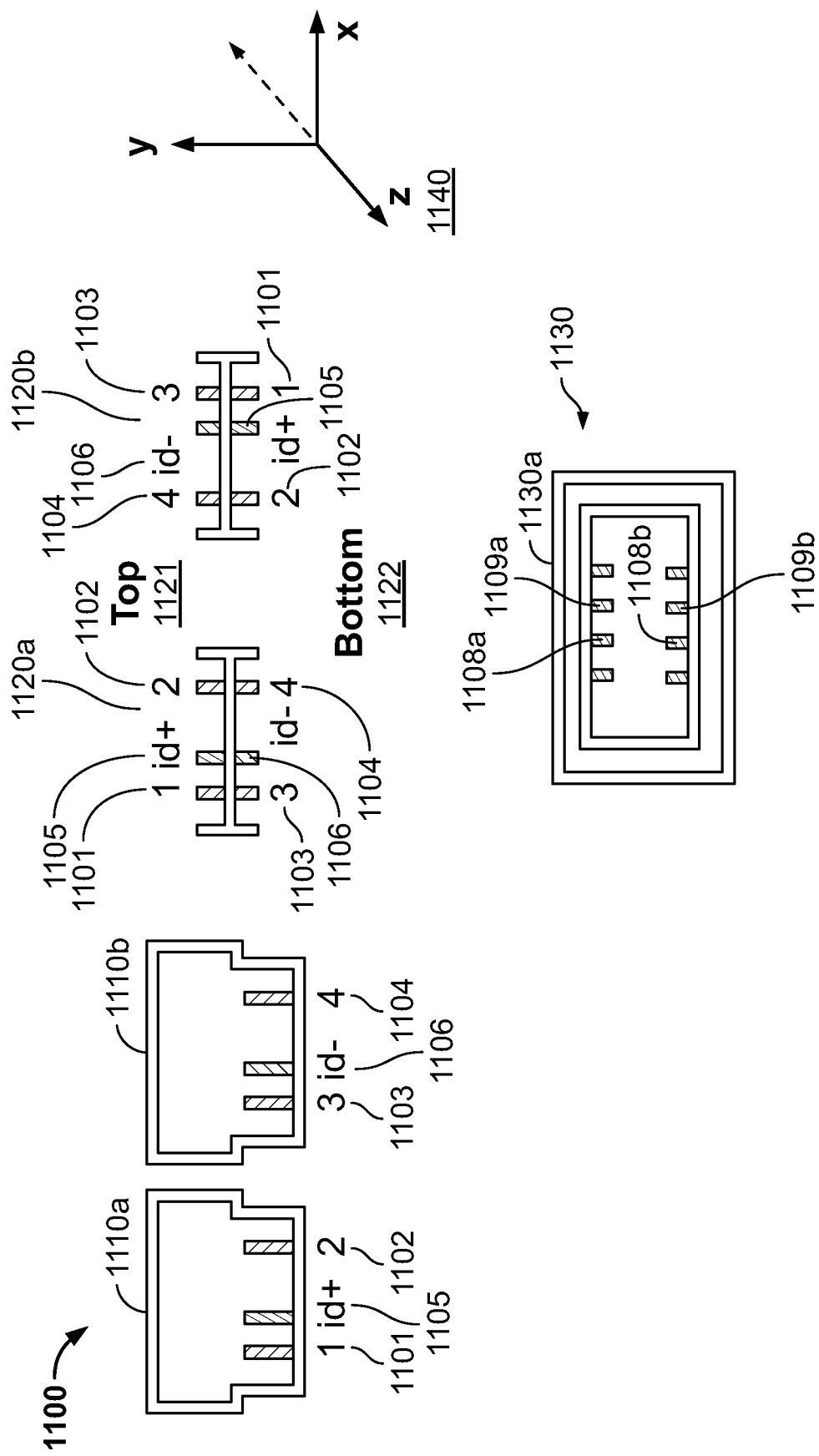
FIG. 11 illustrates a connector which can be used in dual orientations in accordance with another embodiment of the present specification.

FIG. 11 illustrates a connector 1100 which can be used in dual orientations in accordance with another embodiment of the present specification. A first side 1110a and a second side 1110b of a connector 1100 are depicted in FIG. 11. The connector 1100 comprises four output signal pins 1101, 1102, 1103 and 1104 and two ID pins 1105 and 1106. The first side 1110a comprises the output signal pins 1101 and 1102 and the ID pin 1105. The second side 1110b comprises the output signal pins 1103 and 1104 and the ID pin 1106.

The connector 1100 can be coupled to the receiving unit or socket 1130 in two different orientations. A first front-on view 1120a depicts the first side 1110a of the connector 1100 oriented to a 'top' surface 1121 and the second side 1110b oriented to a 'bottom' surface 1122. View 1120a of the connector 1100 depicts the positioning of the various output signal pins and the ID pins in a first orientation, with output signal pins 1101 and 1102 and ID pin 1105 positioned on said 'top' surface 1121 and output signal pins 1103 and 1104 and ID pin 1106 positioned on said 'bottom' surface 1122. A second front-on view 1120*b* depicts the second side 1110*b* of the connector 1100 oriented to said 'top' surface 1121 and the first side 1110*a* oriented to said 'bottom' surface 1122. View 1120*b* depicts the positioning of the various output signal pins and the ID pins in a second orientation, with output signal pins 1103 and 1104 and ID pin 1106 positioned on said 'top' surface 1121 and output signal pins 1101 and 1102 and ID pin 1105 positioned on said 'bottom' surface 1122. In the second view 1120*b*, the connector 1100 is rotated 180 degrees about its horizontal axis or Z axis 1140 as compared to its position in the first view 1120*a*.

When the connector 1100 is inserted in the receiving unit 1130, the various output signal pins and the ID pins of the connector 1100 establish contact with the various mating sockets or pins in the receiving unit 1130. In the system disclosed in FIG. 11, the receiving unit 1130, shown in a front-on view 1130*a*, detects the orientation of the connector 1100 based on the location of the ID pins 1105 and 1106. When the connector 1100 is inserted in the receiving unit 1130 in the first orientation, as shown in view 1120*a*, the ID pin 1105 establishes contact with the ID input pin 1109*a* and the ID pin 1106 establishes contact with the ID input pin 1109*b* of the receiving unit 1130. Alternatively, when the connector 1100 is inserted in the receiving unit 1030 in the second orientation, as shown in view 1120*b*, the ID pin 1105 establishes contact with the ID input pin 1108*a* and the ID pin 1106 establishes contact with the ID input pin 1108*b* of the receiving unit 1130. The system verifies the positions of the ID pins 1105 and 1106 and detects the orientation of the connector 1100 as inserted in the receiving socket 1130 based on these positions. Subsequently, the system reconfigures itself to automatically map each input with its corresponding input channel.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in neuromonitoring procedures may be applied to systems, devices, and methods to be used in other types of medical procedures for monitoring or treatment of diseases.

Variations and modifications will occur to those of skill in the art after reviewing this disclosure. The disclosed features may be implemented, in any combination and sub-combination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A neuromonitoring system comprising:
   a plurality of connectors, wherein each connector in the plurality of connectors is associated with a unique identification code and wherein each connector in the plurality of connectors is coupled to electrodes; and
   a receiving unit configured to receive each connector of the plurality of connectors, to identify the unique identification code associated with each connector of the plurality of connectors, and to associate the electrodes coupled to each connector of the plurality of connectors with a corresponding input channel based on the unique identification code.

2. The neuromonitoring system of claim 1, wherein all electrodes associated with a same unique identification code have a common monitoring functionality type or a common deployment location.

3. The neuromonitoring system of claim 1, wherein the electrodes are divided into groups of electrodes, wherein each group of the group of electrodes is coupled to one connector of the plurality of connectors, and wherein all electrodes in each group of the group of electrodes have a common monitoring functionality type or a common deployment location.

4. The neuromonitoring system of claim 1, wherein each connector in the plurality of connectors comprises an electronically accessible memory and wherein the unique identification code is stored in the electronically accessible memory.

5. The neuromonitoring system of claim 4, wherein the unique identification code is in a 128 bit GUID format.

6. The neuromonitoring system of claim 1, wherein the receiving unit comprises a plurality of input sockets and wherein each input socket of the plurality of input sockets is configured to receive at least one connector of the plurality of connectors.

7. The neuromonitoring system of claim 6, wherein each connector of the plurality of connectors is configured to be coupled to any input socket of the plurality of input sockets.

8. The neuromonitoring system of claim 1, wherein each connector of the plurality of connectors comprises an output pin which is configured to transmit data representative of the unique identification code to the receiving unit.

9. The neuromonitoring system of claim 1, wherein the data representative of the unique identification code is formatted as a bar code or a radio frequency code.

10. The neuromonitoring system of claim 1, wherein each connector of the plurality of connectors has dip switches comprising resistors.

11. The neuromonitoring system of claim 1, wherein each connector of the plurality of connectors is configured to be inserted in the receiving unit using at least two different orientations.

12. The neuromonitoring system of claim 1, wherein each connector of the plurality of connectors comprises at least two designated output pins which are configured to transmit data representative of the unique identification code and data representative of an orientation of the connector to the receiving unit.

13. The neuromonitoring system of claim 12, wherein the at least two designated output pins are configured to be maintained at different polarities or different voltage levels to indicate the orientation of the connector as inserted in the receiving unit.

14. The neuromonitoring system of claim 12, wherein a physical position of the at least two designated output pins is different in each of two orientations.

15. The neuromonitoring system of claim 1, wherein the electrodes are divided into groups of electrodes, wherein each group of the group of electrodes is coupled to one connector of the plurality of connectors, wherein all electrodes in each group of the group of electrodes have a common monitoring functionality type or a common deployment location, and wherein each group of the groups of electrodes has 4, 6, 8, 10, 12 or 16 electrodes.

16. A neuromonitoring system comprising:

a plurality of connectors, wherein each connector in the plurality of connectors is associated with a unique identification code, wherein each connector in the plurality of connectors is coupled to electrodes, wherein the electrodes are divided into groups of electrodes, wherein each group of the group of electrodes is coupled to one connector of the plurality of connectors, and wherein all electrodes in each group of the group of electrodes have a common monitoring functionality type or a common deployment location; and a receiving unit configured to receive each connector of the plurality of connectors, to identify the unique identification code associated with each connector of the plurality of connectors, and to associate the electrodes coupled to each connector of the plurality of connectors with a corresponding input channel based the unique identification code, wherein the receiving unit comprises a plurality of input sockets and wherein each input socket of the plurality of input sockets is configured to receive any connector of the plurality of connectors.

17. The neuromonitoring system of claim 16, wherein each connector in the plurality of connectors comprises an electronically accessible memory and wherein the unique identification code is stored in the electronically accessible memory.

18. The neuromonitoring system of claim 17, wherein the unique identification code is in a 128 bit GUID format.

19. The neuromonitoring system of claim 16, wherein each connector of the plurality of connectors comprises an output pin which is configured to transmit data representative of the unique identification code to the receiving unit.

20. The neuromonitoring system of claim 16, wherein each connector of the plurality of connectors is configured to be inserted in the receiving unit using at least two different orientations.

* * * * *